United States Patent

Scarfone

[11] Patent Number: 5,683,412
[45] Date of Patent: Nov. 4, 1997

[54] FORCE-LIMITING CONTROL MEMBER FOR ENDOSCOPIC INSTRUMENTS AND ENDOSCOPIC INSTRUMENTS INCORPORATING SAME

[75] Inventor: Frank A. Scarfone, Boca Raton, Fla.

[73] Assignee: Symbiosis Corporation, Miami, Fla.

[21] Appl. No.: 363,760

[22] Filed: Dec. 23, 1994

[51] Int. Cl.$^6$ ............................................. A61B 17/28
[52] U.S. Cl. .................................. 606/205; 606/206
[58] Field of Search ............................ 606/205, 206, 606/207, 208, 171, 170, 180; 128/751

[56] References Cited

U.S. PATENT DOCUMENTS

| | | | |
|---|---|---|---|
| H1028 | 3/1992 | Falk et al. | 606/205 |
| 804,229 | 11/1905 | Hutchinson | 606/206 |
| 1,754,806 | 4/1930 | Stevenson | 606/174 |
| 2,060,366 | 10/1936 | Dunlap | 606/206 |
| 3,504,460 | 4/1970 | Solberg | 52/98 |
| 3,855,786 | 12/1974 | Yamamoto | 58/88 |
| 4,085,743 | 4/1978 | Yoon | 606/206 |
| 4,263,900 | 4/1981 | Nicholson | 600/202 |
| 4,522,206 | 6/1985 | Whipple et al. | 606/174 |
| 4,712,545 | 12/1987 | Honkanen | 606/184 |
| 4,760,848 | 8/1988 | Hasson | 606/206 |
| 4,803,983 | 2/1989 | Siegel | 606/151 |
| 4,896,678 | 1/1990 | Ogawa | 128/751 |
| 4,953,559 | 9/1990 | Salerno | 128/751 |
| 4,994,024 | 2/1991 | Falk | 604/22 |
| 5,000,191 | 3/1991 | Reiss et al. | 128/757 |
| 5,009,661 | 4/1991 | Michelson | 606/205 |
| 5,147,356 | 9/1992 | Bhata | 606/37 |
| 5,147,380 | 9/1992 | Hernandez et al. | 606/207 |
| 5,192,298 | 3/1993 | Smith et al. | 606/170 |
| 5,201,759 | 4/1993 | Ferzli | 606/170 |
| 5,219,357 | 6/1993 | Honkanen et al. | 606/205 |
| 5,235,966 | 8/1993 | Jamner | 600/204 |
| 5,250,056 | 10/1993 | Hasson | 606/151 |
| 5,250,073 | 10/1993 | Cottone, Jr. | 606/206 |
| 5,268,605 | 12/1993 | Miller, Jr. | 606/170 |
| 5,281,230 | 1/1994 | Heidmueller | 606/127 |
| 5,286,255 | 2/1994 | Weber | 606/170 |
| 5,304,203 | 4/1994 | El-Mallawany et al. | 606/170 |
| 5,389,104 | 2/1995 | Hahnen et al. | 606/174 |
| 5,395,375 | 3/1995 | Turkel et al. | 606/83 |

FOREIGN PATENT DOCUMENTS

| | | | |
|---|---|---|---|
| 2713386 | 11/1978 | Germany | 606/205 |
| 4313903 | 9/1994 | Germany | 606/205 |

*Primary Examiner*—Michael Buiz
*Assistant Examiner*—Patrick W. Rasche
*Attorney, Agent, or Firm*—David P. Gordon

[57] ABSTRACT

A force-limiting control member for an endoscopic instrument is a flexible wire having a proximal and a distal end, wherein a portion of the wire is bent into a sinusoidal or coiled shape to form a spring portion of the control member. An endoscopic instrument incorporating the force-limiting control member includes a flexible coil having a proximal and a distal end, a pair of forceps jaws mounted for rotation on a clevis which is coupled to the distal end of the coil, and a proximal handle coupled to the proximal end of the coil. The proximal handle has a spring biased lever coupled to it in a manner which limits the throw of the lever to a preselected distance. The force-limiting control member extends through the coil and is coupled at its distal end to the forceps jaws and at its proximal end to the actuating member. The spring portion of the control member which preferably resides inside the handle and is free to expand as the actuating member is moved from its spring biased first position to its throw limited second position. The spring portion of the control member is formed to have a spring constant such that when the actuation member is in its second throw limited position, the spring portion is expanded to a length which causes it to exert a predetermined force without exceeding its elastic limit. This is advantageously accomplished by pre-stressing the spring.

21 Claims, 6 Drawing Sheets

FORCE-LIMITING CONTROL MEMBER FOR ENDOSCOPIC INSTRUMENTS AND ENDOSCOPIC INSTRUMENTS INCORPORATING SAME

BACKGROUND OF THE INVENTION

1. Field of the Invention

This invention relates broadly to endoscopic instruments. More particularly, this invention relates to force limiting control members for an endoscopic instrument.

2. State of the Art

Endoscopic surgery involves the insertion of an endoscope and/or an endoscopic surgical instrument through a body cavity. Most endoscopic instruments have similar configurations, with a hollow member, a control member which extends through the hollow member, a proximal handle having an actuating member coupled to the control member, and distal end effectors which are coupled to the control member. (As used herein, "proximal" means closest to the surgeon and furthest from the surgical site, while "distal" means furthest from the surgeon and closest to the surgical site.) The control member is typically either a push rod or a pull wire, and the hollow member is typically either a tube or a flexible coil. The end effectors take many forms such as grippers, cutters, forceps, dissectors and the like. The actuating member moves the control member to open and close the end effectors. When the tool is inserted into the body of the patient, the surgeon often locates the end effectors with the aid of the endoscope and operates the tool with the actuating member while holding the handle.

It is expected that in 1996 more than two million endo-surgeries will be performed which, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year.

Initially, endoscopic surgical instruments were very expensive. Recently, however, disposable endoscopic instruments have reduced the cost of endoscopic surgery dramatically. Disposable endoscopic instruments generally compromise durability to reduce the cost of manufacture. It is essential, however, that the instrument be durable enough so that it does not break during the first and only procedure in which it will be used. Generally, disposable instruments are strong enough to survive at least one and often several procedures. However, it is always a concern that an endoscopic instrument might break during a procedure and that sharp metallic pieces of the instrument will become lodged inside the body of the patient. In the case of endoscopic grippers and forceps, in particular, it is important that the surgeon does not apply too much force to the end effectors of the instrument, lest they break while inside the body of the patient.

The problem of accidental breakage of endoscopic instruments while in use has been addressed in the prior art. Different approaches have been taken to limit the amount of force which may be applied to the end effectors by the surgeon. In the case of instruments having a rigid tube and push rod, it is known to provide the push rod with a frangible link portion so that the push rod will break before the end effectors break. Exemplary frangible link push rod arrangements are disclosed in U.S. Pat. No. 4,896,678 to Ogawa and in co-owned allowed applications Ser. No. 07/978,249, filed Nov. 18, 1992, and Ser. No. 08/101,190 filed Aug. 3, 1993. Another type of frangible link known in the art is disclosed in U.S. Statutory Invention Registration No. H1028 to Falk et al. which discloses an endoscopic instrument having a handle with a frangible actuating member. It has also been known in the art to use springs to limit the force which may be applied to end effectors. U.S. Pat. No. 5,286,255 to Weber discloses a rather complicated arrangement of levers and compression springs in the handle of a surgical forceps having a rigid tube and push rod.

Successful use of a force limiting spring or frangible link in an endoscopic instrument having a flexible coil and pull wire is unknown in the art.

SUMMARY OF THE INVENTION

It is therefore an object of the invention to provide a force-limiting control member for an endoscopic instrument which is suitable for use in an instrument having a pull wire control member.

It is also an object of the invention to provide a force-limiting control member for an endoscopic instrument which utilizes a spring to limit the force which may be applied to the end effectors of the instrument.

It is another object of the invention to provide a force-limiting control member which is easy and inexpensive to manufacture.

It is still another object of the invention to provide an endoscopic instrument which incorporates the force-limiting control member of the invention.

In accordance with the objects of the invention which will be discussed in detail below, a force-limiting control member for an endoscopic instrument is provided. The force-limiting control member is a flexible wire, having a bent, pre-stressed portion which constitutes a spring portion of the control member. Preferably, the flexible wire is bent into a sinusoidal shape to form the spring portion near the proximal end of the wire.

An endoscopic instrument incorporating the force-limiting control member is also provided, and includes a flexible coil through which the force-limiting control member extends, a pair of forceps jaws mounted for rotation on a clevis which is coupled to a distal end of the coil, and a proximal handle coupled to a proximal end of the coil. The proximal handle has a spring biased actuating member pivotally coupled to it in a manner which limits the throw of the actuating member to a preselected distance. The force-limiting control member is coupled at its distal end to the forceps jaws and at its proximal end to the actuating member. The sinusoidal spring portion of the control member preferably resides inside the handle and is free to expand as the actuating member is moved from its spring biased first position to its throw limited second position. The spring portion of the control member is formed to have a spring constant such that when the actuation member is in its second throw limited position, the spring portion is expanded to a length which causes it to exert a predetermined force which is less than the pre-stressing force. This guarantees that even after repeated use, the spring portion of the control member will not be permanently deformed, and that the jaws will continue to properly open and close. In addition, this arrangement guarantees that the force exerted on the jaws will always be limited to the force exerted by the spring, which in turn is preselected so that the jaws will never be subjected to a force which could cause them to break. According to a preferred aspect of the invention, the spring constant and the shape of the spring are chosen so that the force exerted on the jaws is always less than or equal to about fifteen pounds. The invention is also disclosed in conjunction with an otherwise conventional endoscopic biopsy forceps instrument.

Additional objects and advantages of the invention will become apparent to those skilled in the art upon reference to the detailed description taken in conjunction with the provided figures.

DETAILED DESCRIPTION OF THE PREFERRED EMBODIMENT

Figure 1:
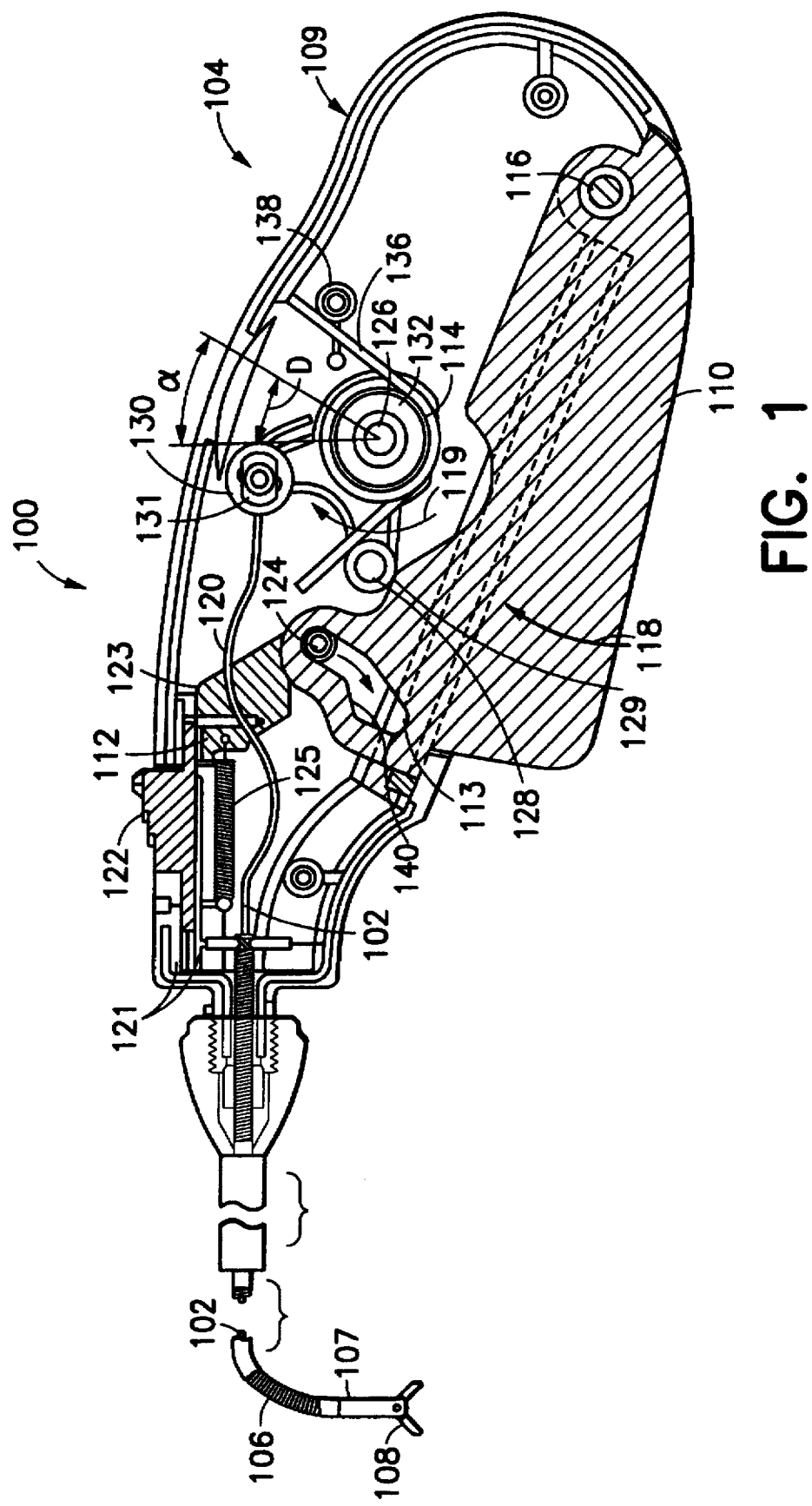
FIG. 1 is a broken side elevational partially transparent and partially sectional view of a cardiac forceps instrument incorporating the first embodiment of the force limiting pull wire of the invention with the forceps in the open position.
Figure 2:
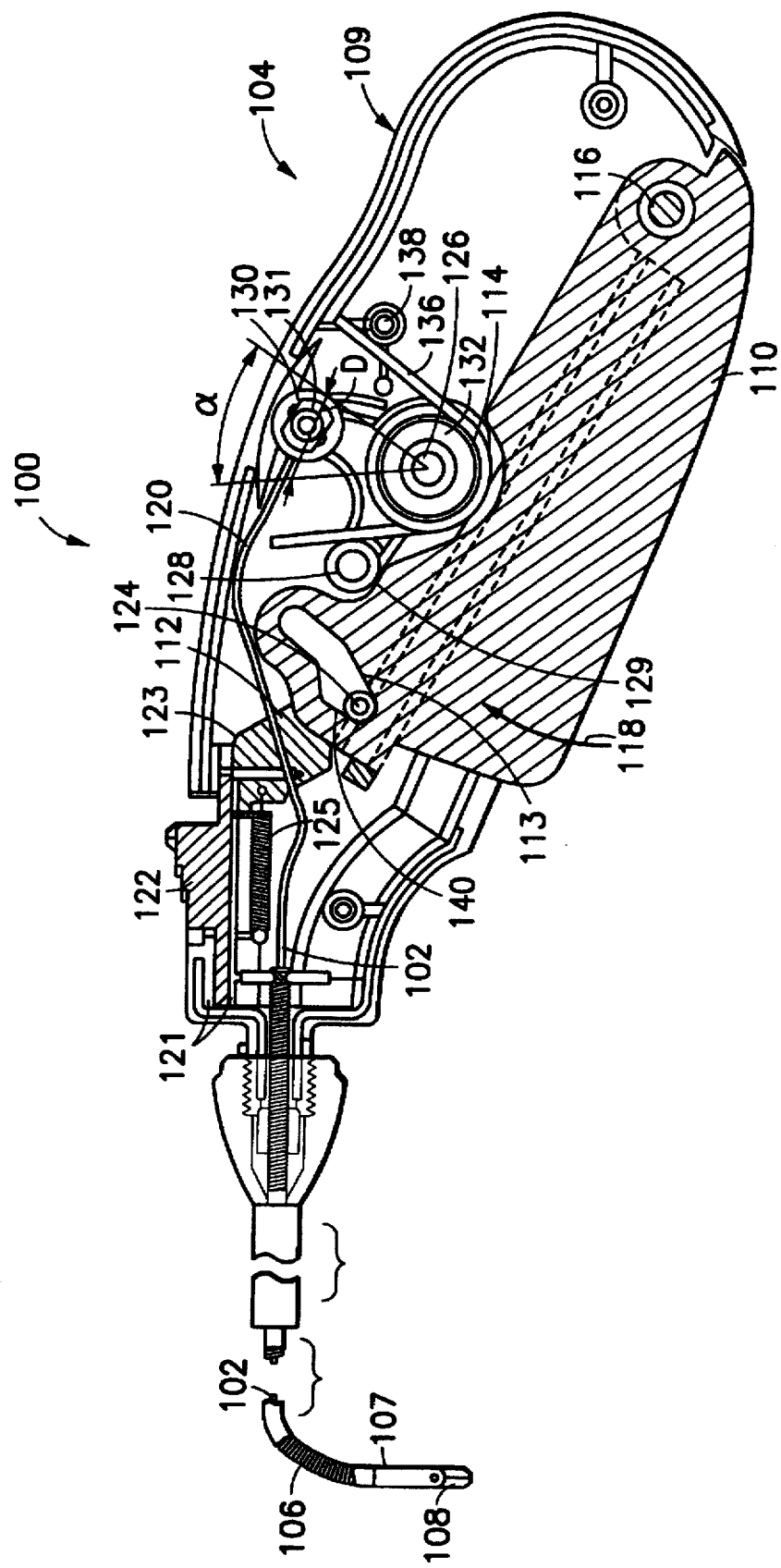
FIG. 2 is a broken side elevational partially transparent and partially sectional view of a cardiac forceps instrument incorporating the first embodiment of the force limiting pull wire of the invention with the forceps in the closed position.
Figure 3:
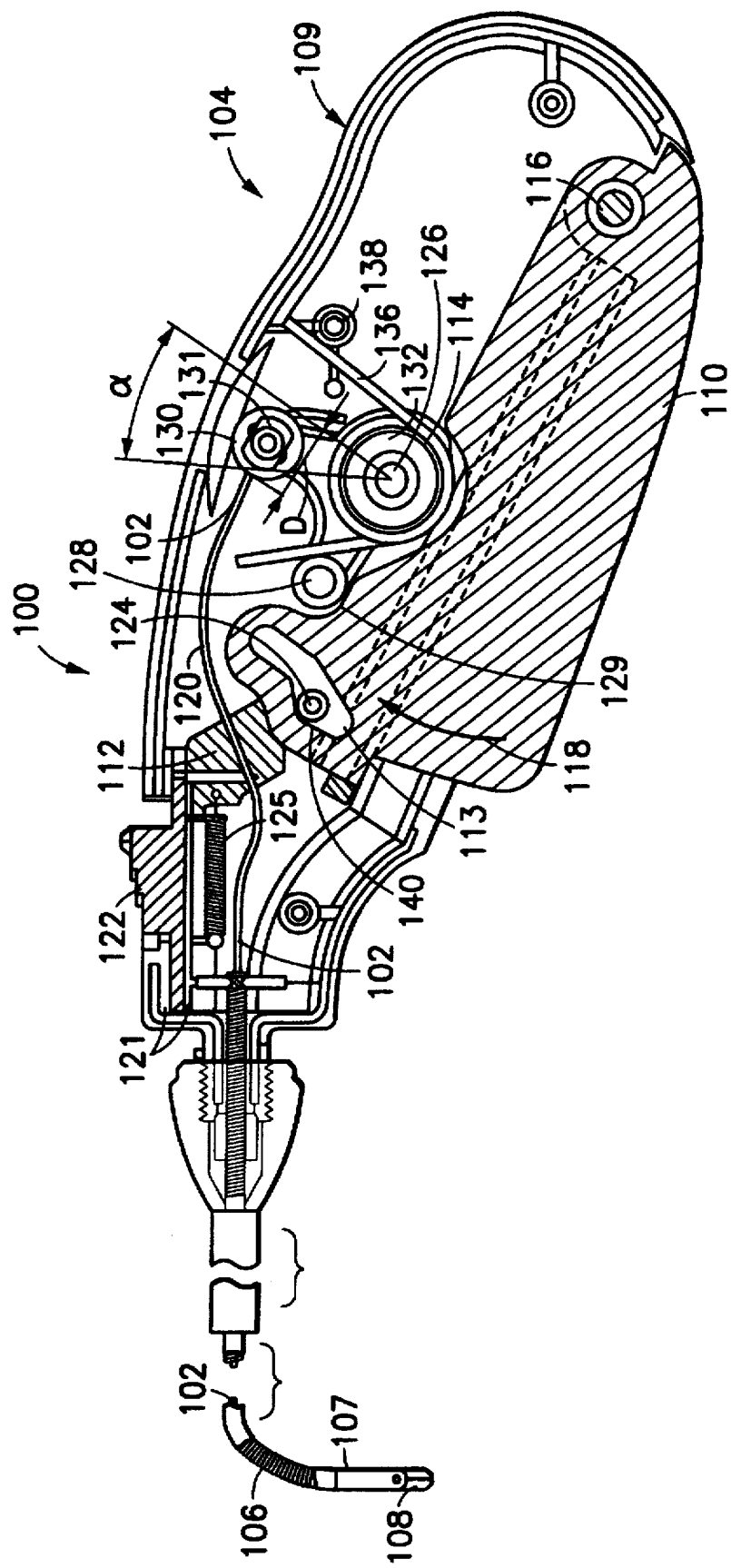
FIG. 3 is a broken side elevational partially transparent and partially sectional view of a cardiac forceps instrument incorporating the first embodiment of the force limiting pull wire of the invention with the forceps in an intermediate locked position.

FIGS. 1-3, show an endoscopic instrument 100 incorporating a first embodiment of the force-limiting control member 102 according to the invention. The endoscopic instrument 100 is a cardiac forceps and generally includes a proximal handle assembly 104 coupled to the proximal end of a flexible coil 106 and a pair of forceps jaws 108 which are mounted on a clevis 107 coupled to the distal end of the coil 106. The force-limiting control member 102 is a relatively flexible pull wire which extends through the coil and is coupled to the forceps jaws 108 at its distal end. The proximal end of the control member 102 is coupled to the handle assembly as described below, and a portion of the control member close to its proximal end is formed as a pre-stressed sinusoidal spring 120.

The handle assembly 104 includes a handle casing 109 which is shaped to fit comfortably in the surgeon's palm, an actuating member or lever 110 which is positioned for gripping by the surgeon's fingers, a spring biased locking switch assembly 112 which is movable by the surgeon's thumb, and a lever biasing assembly 114 which biases the lever 110 to a first position shown in FIG. 1. The lever 110 is pivotally coupled to the handle casing 109 by a proximal axle 116, and the lever is provided with a bifurcated portion having distal slots 113 with steps 140. The locking switch assembly 112 has a sliding knob 122, which rides in a slot 121 in the casing 109, and a lower flange 123 having a pin 124 which engages and rides in the slots 113 of the lever 110. A tension spring 125 biases the locking switch assembly 112 in the distal direction. The lever biasing assembly 114 has a hub 132 with first and second radial extensions 128, 130, and a coil spring 136. The hub 132 is pivotally mounted on an upstanding axle pin 126 of the casing 109. The coil spring 136 surrounds the hub 132 and engages the first radial extension 128 as well as an upstanding pin 138 in the housing 109 so as to bias the entire lever biasing assembly 114 in a distal and downward direction so that the radial extension 128 abuts against the lever 110 at surface 129 and biases the lever to the position shown in FIG. 1. The second radial extension 130 is provided with a metal coupling member 131 to which the proximal end of the pull wire 102 is connected.

FIG. 1 shows the cardiac forceps 100 in an "open" position. In this position, no force is applied to the pull wire 102 and the forceps jaws 108 are open. The lever 110 is biased outward from the casing 109 by the spring 136 and held in position by its engagement with the casing 109. The spring biased locking switch 112 is held in the proximal position against the force of spring 125 by the stepped slots 113 in the lever 110.

Referring now to FIGS. 1 and 2, when the lever 110 is pressed into the casing 109, it pivots about the axle 116 in the direction indicated by the arrow 118. The lever 110 engages the first radial extension 128 of the lever biasing assembly 114 and causes the lever biasing assembly to rotate about the axle 126 in the direction shown by the arrow 119 as the radial extension 128 rides on the surface 129 of the lever. As the lever biasing assembly is rotated, the second radial extension 130 is moved in a proximal direction which moves the pull wire 102 proximally to effect a closing of the forceps jaws 108. Simultaneously, as the lever 110 is moved in the direction indicated by arrow 118, the stepped slots 113 are moved relative to the pin 124 until the pin is forced to enter the steps 140 in slots 113 by the action of the spring 125 which moves the switch assembly 112 in the distal direction. After the lever 110 has moved a certain distance, further movement is prevented by the pin 124 which engages the bottom of the slots 113 (with movement of the proximal end of the sliding knob 122 constrained by the slot 121 in the handle casing 109). Thus, the maximum movement or throw of the pull wire 102 in the proximal direction is also limited to the distance D which is the cord length of the circular arc path of the radial extension 130 through the angle α. As the pull wire 102 is moved from the position shown in FIG. 1 to the position shown in FIG. 2, the spring portion 120 of the pull wire control member 102 is extended such that the maximum amount of force applied to the forceps jaws 108 is determined by the force exerted by the spring portion 120. As described in more detail below, the spring portion 120 of the pull wire 102 is dimensioned so that the force applied to the forceps jaws 108 will never exceed a predetermined maximum force. It will be appreciated that the forceps Will remain in the position shown in FIG. 2 only so long as the actuating member 110 is pressed firmly against the radial extension 128 of the lever biasing assembly 114.

In addition to the fully open position shown in FIG. 1, and the fully closed position shown in FIG. 2, the cardiac forceps 100, according to the invention, is provided with a mechanism for maintaining the forceps in an intermediate position which is shown in FIG. 3.

Turning now to FIG. 3, when the lever 110 is released from the position shown in FIG. 2, the spring 136 causes the lever biasing assembly to rotate in the direction opposite arrow 118. This pushes the lever 110 in the same direction (opposite the arrow 118) and the stepped slots 113 move relative to the pin 124. Because the pin 124 is now in a distal position due to the action of the spring 125, it resides under the steps 140 in the slots 113. Thus, when the lever 110 reaches the position shown in FIG. 3, where the steps 140 abut the pin 124, further movement of the lever 110 is halted by the pin 124. In this position, the spring portion 120 of the pull wire 102 is still extended somewhat and still exerts some force (albeit a lesser force) on the forceps jaws 108. In this intermediate position, the jaws are held closed with a lesser predetermined force by the spring portion 120 of the pull wire 102.

Referring now to FIGS. 1 and 3, it will be appreciated that when the push knob 122 is pushed back in the proximal direction, the pin 124 of the locking switch assembly 122 is moved out of the steps 140 in the slots 113 against the bias of the spring 125. When the pin 124 is moved proximally relative to the step 140, movement of the lever 110 in the direction opposite to the arrow 118 is no longer halted. The spring 136 continues to bias the lever via the lever biasing assembly 114, and the lever 110 is moved into the fully open position shown in FIG. 1.

Referring generally now to FIGS. 1–3, it will be appreciated that the amount of force applied to the forceps jaws 108 by the spring portion 120 of the pull wire 102 will be determined by the spring constant of the spring portion 120 and the distance through which the pull wire is pulled. According to Hooke's law, the force F exerted by a spring when it is displaced through a distance x from its at rest length is the product of its spring constant k and its displacement x ($F=-kx$, where the negative is a vector direction indicator). Similarly, if a force F' is applied to a spring having a constant k, the spring will be displaced a distance x, such that $x=F'/k$. Applying Hooke's law to the present invention, it will be understood that as force is applied to the actuating member 110, the force limiting spring portion 120 of the pull wire 102 will be displaced proximally some distance x. However, the distance x which the pull wire may be displaced is limited to the distance D through which the lever biasing assembly 114 may move the pull wire as described above. Therefore, no matter how much force is applied to the actuating member 110, the pull wire will never be displaced more than the distance D, and the maximum force applied by the spring portion 120 of the pull wire 102 will never exceed $-kD$.

According to the invention, the spring portion 120 of the pull wire 102 is formed in such a way that it will not be permanently deformed during use, and that it will return to its original shape so that each time it is displaced through distance D, substantially the same force will be applied to the forceps jaws. The shape and displacement of the spring portion 120 of the pull wire 102 are shown in greater detail in FIGS. 4 and 5.

Figure 4:
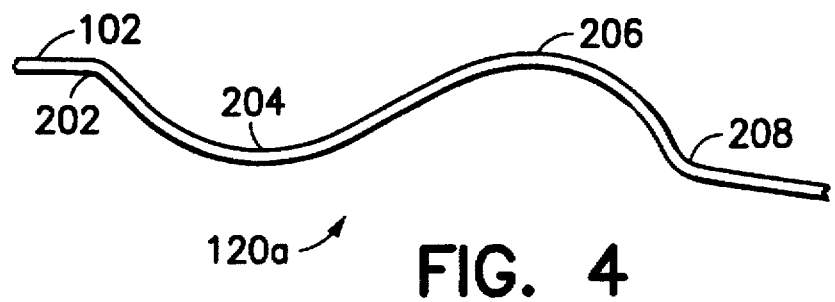
FIG. 4 is a side elevation view of the force-limiting spring portion of the pull wire in a first stage of manufacture prior to pre-stressing according to the invention.

Turning now to FIG. 4, the spring portion 120 of the pull wire 102 is shown to be provided with a sinusoidal shape. According to the invention, the pull wire is formed from stainless steel and the spring portion 120 is formed by bending a proximal portion of the pull wire over different radii in four locations 202, 204, 206, 208 in order to form a sine wave shape. An important aspect of the invention, however, is that after the proximal portion of the pull wire is bent into a sine wave shaped spring portion 120, the spring portion is subjected to a stressing load of, e.g., approximately twenty-five pounds. By subjecting the spring portion to a stressing load, the spring portion is prestressed so that it will not be permanently deformed by any force substantially less than the stressing load of twenty-five pounds. The results of pre-stressing the spring portion of the pull wire can be appreciated by a comparison of the post-pre-stressing configuration of FIG. 5 and the prior-to-pre-stressing configuration of FIG. 4.

Figure 5:
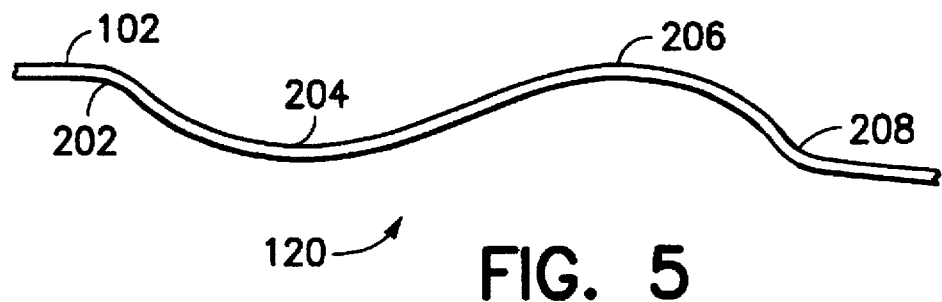
FIG. 5 is a side elevation view of the force-limiting spring portion of the pull wire according to the invention after pre-stressing as it appears when the forceps of the biopsy forceps instrument are open.

According to a presently preferred embodiment of the pull wire as used in the cardiac forceps instrument described above, a 0.027 inch diameter pull wire 102 is used. During the first stage of manufacture, the spring portion 120a is formed by bending a sinusoidal shape form having a length of about 1.5 inches into the wire 102 beginning at a point 202 approximately two to three inches distal of the proximal end of the wire 102. After the wire is bent, the spring portion 120a is subjected to a twenty-five pound stressing force which extends and permanently deforms the spring portion to the shape shown in FIG. 5. After this pre-stressing, the spring portion 120 which is formed is elongated by approximately one tenth of one inch (relative to its previous shape of FIG. 4) due to a slight increase in the radii of the bends in the spring 120 (relative to 120a). The resulting spring portion 120 as described with reference to FIG. 5 is substantially the state of the spring portion 120 when the forceps described above are in the open position as shown in FIG. 1.

Figure 6:
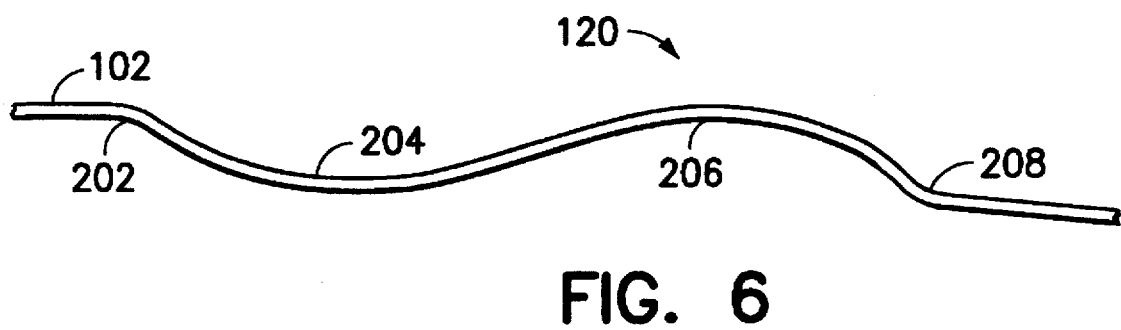
FIG. 6 is a side elevation view of the force-limiting spring portion of the pull wire according to the invention as it appears when stressed by the actuating member of the forceps instrument.

When the spring portion 120 is stretched by the action of the actuating member as described above with reference to FIG. 2, it assumes a shape as shown in FIG. 6. Because the spring portion cannot be stretched through a distance more than D as described above, the force applied to the spring by the lever cannot be more than kD where k is the spring constant. Given the spring described above and a limiting distance D of approximately 0.3 inches, the maximum force which will be exerted by the spring is approximately fifteen pounds.

While the presently preferred embodiment of the spring portion of the pull wire is a sinusoidal shaped spring, other spring shapes can be utilized. By way of example and not limitation, a coil spring such as shown in FIGS. 7–9 can be utilized.

Figure 7:
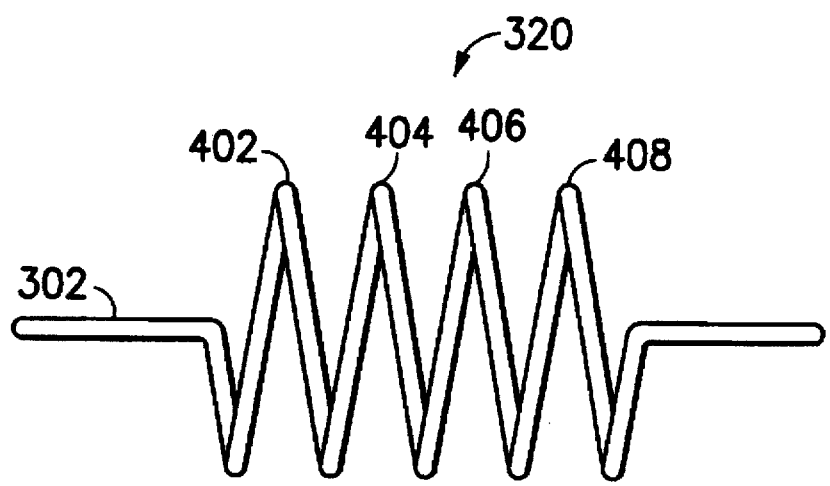
FIG. 7 a view similar to FIG. 4 of a second embodiment of the force-limiting spring portion of the pull wire according to the invention.
Figure 8:
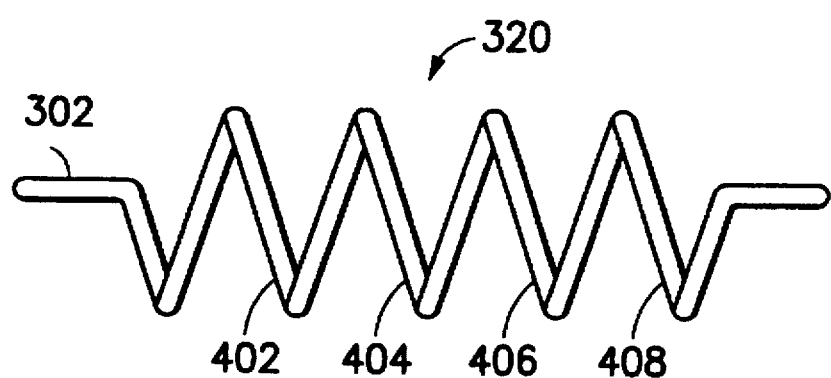
FIG. 8 a view similar to FIG. 5 of a second embodiment of the force-limiting spring portion of the pull wire according to the invention.
Figure 9:
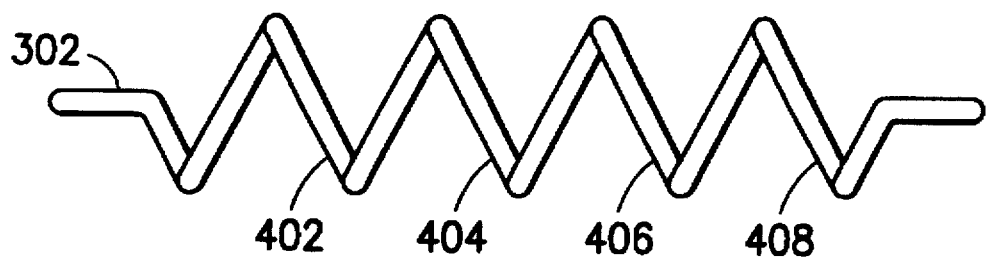
FIG. 9 a view similar to FIG. 6 of a second embodiment of the force-limiting spring portion of the pull wire according to the invention.

Turning now to FIGS. 7 through 9, a coil spring portion 320 of a pull wire 302 can be formed by winding a portion of the pull wire around a mandrel to form several coil turns, e.g. 402, 404, 406, 408. Depending upon the properties of the wire, enough coils can be formed such that the coiled spring portion need not be subjected to pre-stressing, as the coils will stretch the entire permitted throw or displacement distance without permanently deforming; i.e., exceeding the elastic limit of the coil. However, if desired or necessary, a coiled spring portion can be subjected to a pre-stressing load until it permanently deforms as indicated by FIG. 8. In either case, the spring 320 will have a spring constant k such that when displaced by an amount x as shown in FIG. 9, it will exert a predetermined force of $-kx$, which, if less than its deforming force (which could be due to pre-stressing), will not permanently deform the spring.

Figure 10:
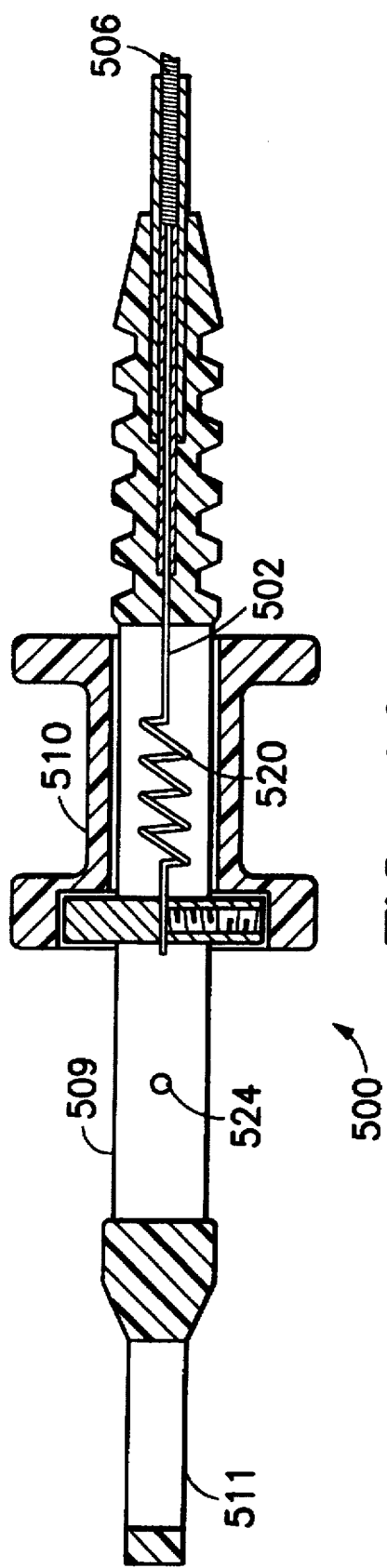
FIG. 10 is a longitudinal cross sectional view of a conventional biopsy forceps handle incorporating a force-limiting control member according to the invention and showing the actuating member in the "jaws open" position.
Figure 11:
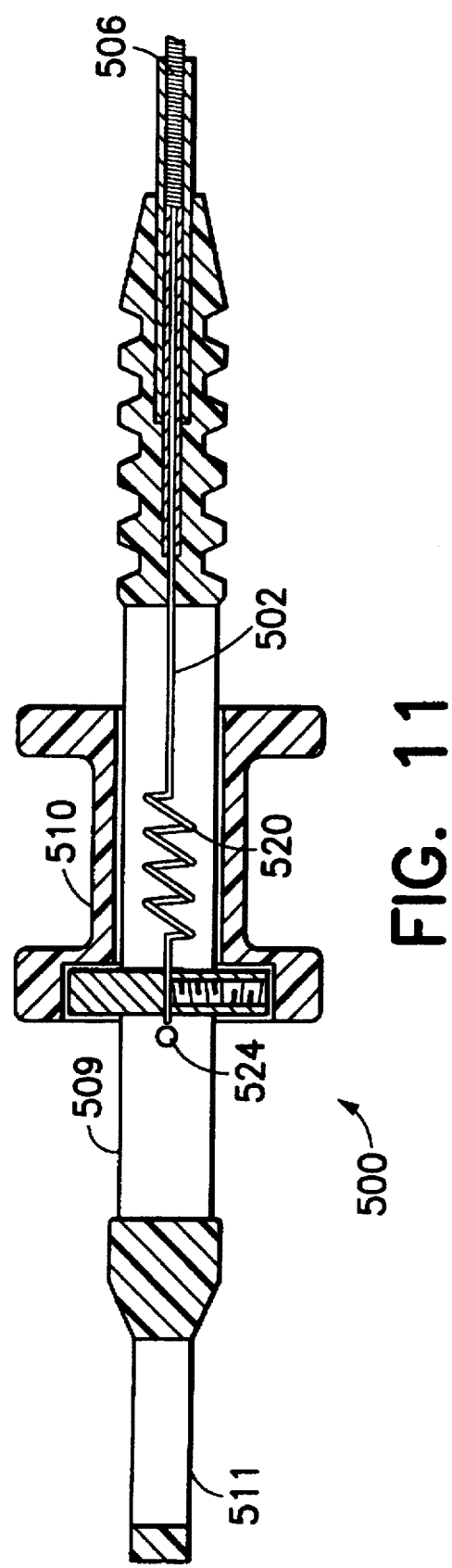
FIG. 11 is a view similar to FIG. 10 showing the actuating member in the "jaws closed" position.

FIGS. 10 and 11 show a conventional biopsy forceps handle 500 utilizing a force-limiting pull wire 502 according to the invention. Those skilled in the art will appreciate that an endoscopic biopsy forceps typically includes a proximal handle 500, a pair of distal jaws (not shown, but substantially the same as the jaws 108 shown in FIGS. 1–3), and a long flexible coil 506 to which a clevis (not shown) is attached in order to connect the jaws to the handle. The handle 500 includes a slotted shaft 509 having a thumb ring 511 and a displaceable spool 510. A pull wire 502 coupled to the spool 510 extends through the coil 506 and is coupled to the jaws. Movement of the spool relative to the shaft causes opening and closing of the jaws. According to the invention, the pull wire 502 is provided with a force-limiting spring portion 520 which is formed as described above and which functions substantially as described above. In order to limit the distance through which the spring portion may be displaced, a stopping pin 524 is provided on the shaft 509. Thus, when the spool is moved from the position shown in FIG. 10 (the "jaws open" position) to the position shown in FIG. 11 (the "jaws closed" position), further movement of the spool is limited by the stopping pin 524. The spring portion 520, therefore can never be displaced any more than is shown in FIG. 11 and thus the force applied to the jaws will never be more than the force exerted by the spring portion 520 when it is in the position shown in FIG. 11.

There have been described and illustrated herein several embodiments of a force-limiting control member for an endoscopic instrument and endoscopic instruments incorporating a force-limiting control member. While particular embodiments of the invention have been described, it is not intended that the invention be limited thereto, as it is intended that the invention be as broad in scope as the art will allow and that the specification be read likewise. Thus, while a particular cardiac forceps, and a particular biopsy forceps have been disclosed, it will be appreciated that the force-limiting control member according to the invention could be used in other endoscopic instruments as well. Furthermore while particular types of actuating lever members and throw limiting members have been disclosed, it will be understood that other devices can be used to actuate the pull wire as well as to limit the displacement of the spring so than a maximum spring force is never exceeded. By way of example, and not by way of limitation, it will be appreciated that in order to limit displacement of the spring portion, any of several devices or designs may be used. For example, the displacement limiting may simply be a result of the actuating member hitting the interior of the handle casing or the lever biasing assembly. Alternatively, in the case where the actuating lever pivots into the handle, the handle may be designed so that the lever pivots to a point where the exterior portion of the lever is flush with the exterior portion of the handle, thereby precluding further movement of the lever under normal circumstances. In the case of the displaceable spool on the biopsy forceps device, the displacement limiter may be a collar on the shaft rather than a stopping pin. Moreover, the displacement limiter may simply be re-dimensioning the length of the slot in the shaft. Also, while a sinusoidal spring or a coil spring is preferred, it will be recognized that other types of prestressed springs could be used. Moreover, while particular configurations have been disclosed in reference to materials and dimensions of the force-limiting control member it will be appreciated that other materials and dimensions could be used as well. It will therefore be appreciated by those skilled in the art that yet other modifications could be made to the provided invention without deviating from its spirit and scope as so claimed.

I claim:

1. A force-limiting control member for use in an endoscopic instrument, where the endoscopic instrument has a hollow tube member, a pair of end effectors, a handle, and an actuating member, said force-limiting control member comprising:

a flexible wire having a proximal end and a distal end, said flexible wire extending through the tube member, said distal end of said flexible wire being coupled to the end effectors and said proximal end of said flexible wire being coupled to the actuating member such that movement of the actuating member relative to the handle moves the flexible wire through the tube member and causes the end effectors to close, wherein a portion of said flexible wire is bent to form a tension spring and is prestressed prior to coupling said flexible wire to the end effectors and the actuating member.

2. A force-limiting control member according to claim 1, wherein:

said portion of said flexible wire which is bent to form a tension spring is a proximal portion of said flexible wire.

3. A force-limiting control member according to claim 2, wherein:

said tension spring is sinusoidal in shape.

4. A force-limiting control member according to claim 2, wherein:

said tension spring is a coil spring.

5. A force-limiting control member according to claim 1, wherein:

said portion of said flexible wire is prestressed with a force of at least approximately twenty-five pounds.

6. In an endoscopic instrument having a hollow tube member with a proximal and distal end, a pair of end effectors coupled to the distal end of the tube member, a handle coupled to the proximal end of the tube member, a control member, and an actuating member coupled to said control member and movable relative to the handle, so as to cause said control member to move through at most a distance d, the improvement comprising:

said control member having a proximal end and a distal end, said distal end being coupled to the end effectors and said proximal end being coupled to the actuating member such that movement of the actuating member relative to the handle moves said control member through the tube member and causes the end effectors to close, a portion of said control member being formed as a tension spring having an elastic limit which is not exceeded when said tension spring is stretched by the distance d, said tension spring being one of a prestressed spring, a sinusoidal shaped spring, and a coil spring.

7. In an endoscopic instrument according to claim 6, wherein:

said tension spring is a pre-stressed spring.

8. In an endoscopic instrument according to claim 6, wherein:

said portion of said control member being a proximal portion.

9. In an endoscopic instrument according to claim 7, wherein:

said tension spring is sinusoidal in shape.

10. In an endoscopic instrument according to claim 6, wherein:

said tension spring is a coil spring.

11. In an endoscopic instrument according to claim 6, wherein:

said elastic limit of said tension spring is at least approximately twenty-five pounds.

12. In an endoscopic instrument according to claim 6, the improvement further comprising:

stop means for limiting movement of the actuating member such that said control member is limited to moving at most said distance d.

13. In an endoscopic instrument according to claim 12, wherein:

said tension spring has a tension spring constant such that when said spring is stressed by movement of the actuating member until the actuating member contacts said stop means for limiting movement, the force exerted by said tension spring is no more than approximately fifteen pounds.

14. An endoscopic instrument comprising:

a) a hollow tube member having a proximal end and a distal end;

b) a pair of end effectors coupled to said distal end of said tube member, at least one of said end effectors being rotatable relative to the other from an open to a closed position;

c) a handle coupled to said proximal end of said tube member;

d) an actuating member movable relative to said handle;

e) a control member extending through said hollow tube member, said control member having a proximal end and a distal end, said distal end of said control member being coupled to said at least one of said end effectors and said proximal end of said control member being coupled to said actuating member such that movement of said actuating member relative to said handle moves said control member at most a distance d and causes said end effectors to close, wherein a portion of said control member is formed as a tension spring having an elastic limit which is not exceeded when said tension spring is stretched by said distance d, said tension spring being one of a pre-stressed spring, a sinusoidal shaped spring, and a coil spring.

15. An endoscopic instrument according to claim 14, wherein:

said portion of said control member is a proximal portion.

16. An endoscopic instrument according to claim 14, wherein:

said tension spring is a pre-stressed spring.

17. An endoscopic instrument according to claim 16, wherein:

said tension spring is sinusoidal in shape.

18. An endoscopic instrument according to claim 14, wherein:

said tension spring is a coil spring.

19. An endoscopic instrument according to claim 14, wherein:

said elastic limit is at least approximately twenty-five pounds.

20. An endoscopic instrument according to claim 14, further comprising:

f) stop means for limiting movement of said actuating member such that said control member is limited to moving at most said distance d.

21. An endoscopic instrument according to claim 20, wherein:

said tension spring has a spring constant such that when said tension spring is stressed by movement of said actuating member until said actuating member contacts said stop means for limiting movement, the force exerted by said tension spring is no more than approximately fifteen pounds.

* * * * *